United States Patent [19]

Pigerol et al.

[11] 4,057,530
[45] Nov. 8, 1977

[54] 2-PHENYL-INDOLE DERIVATIVES AND PROCESS FOR PREPARING THE SAME

[75] Inventors: Charles Pigerol, Saint-Ouen; Paul de Cointet de Fillain, Sisteron; Souli Nanthavong, Grenoble; Jacques Le Blay, Luisant, all of France

[73] Assignee: Labaz, Paris, France

[21] Appl. No.: 582,915

[22] Filed: June 2, 1975

[30] Foreign Application Priority Data

June 18, 1974 France ............................... 74.21042

[51] Int. Cl.² ................. C07D 209/04; C07D 209/14; C07D 209/18; C08K 5/34
[52] U.S. Cl. ............................ 260/45.8 N; 260/319.1; 260/326.12 R; 260/326.13 R; 260/326.15; 260/326.16
[58] Field of Search ............ 260/45.8 N, 326.14, 260/23 XA, 326.13 R, 326.16, 319.1, 326.12 R, 326.15

[56] References Cited

U.S. PATENT DOCUMENTS

| | | | |
|---|---|---|---|
| 3,467,670 | 9/1969 | Suh | 260/45.8 N |
| 3,491,114 | 1/1970 | Suh | 260/45.8 N |
| 3,629,170 | 12/1971 | Yamanouchi | 260/45.8 N |
| 3,726,898 | 4/1973 | Duncan et al. | 260/326.13 R |
| 3,799,943 | 3/1974 | Bell | 260/326.13 R |
| 3,888,818 | 6/1975 | Deblondre | 260/45.8 N |

Primary Examiner—Donald E. Czaja
Assistant Examiner—H. H. Fletcher
Attorney, Agent, or Firm—Mason, Kolehmainen, Rathburn & Wyss

[57] ABSTRACT

New stabilizers of polymers and co-polymers of vinyl chloride, the said stabilizers being 2-phenyl-indole derivatives corresponding to the formula:

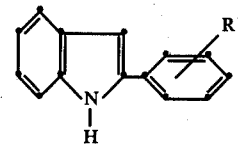

wherein R represents a phenyl radical, an amino group, optionally substituted by an acetyl or benzoyl radical, a mercapto group, optionally substituted by a branched- or straight-chain alkyl group containing from 1 to 12 carbon atoms or by a cyclohexyl radical, a carboxyl radical, a radical represented by the formula:

$R_1O-$ wherein $R_1$ represents a hydrogen atom, an isopropyl, carboxymethyl, carbethoxymethyl, carbethoxyisopropyl, acetyl, docosanoyl, benzoyl, benzyl, or allyl radical or a branched-or straight-chain alkyl radical containing from 6 to 12 carbon atoms.

9 Claims, No Drawings

2-PHENYL-INDOLE DERIVATIVES AND PROCESS FOR PREPARING THE SAME

The present invention relates to 2-phenyl-indole derivatives and to processes for preparing the said 2-phenyl-indole derivatives.

The 2-phenyl-indole derivatives with which the present invention is concerned are those represented by the formula:

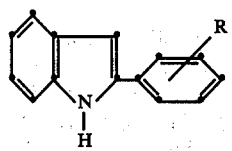   I wherein R represents a phenyl radical, an amino group, optionally substituted by an acetyl or benzoyl radical, a mercapto group, optionally substituted by a branched- or straight-chain alkyl group containing from 1 to 12 carbon atoms or by a cyclohexyl radical, a carboxyl radical, a radical represented by the formula:

$R_1O-$ wherein $R_1$ represents a hydrogen atom, an isopropyl, carboxymethyl, carbethoxymethyl, carbethoxyisopropyl, acetyl, docosanoyl, benzoyl, benzyl, or allyl radical or a branched-or straight-chain alkyl radical containing from 6 to 12 carbon atoms.

The derivatives corresponding to formula I can be prepared, according to the Fischer Indole Synthesis, by reacting a substituted acetophenone represented by the formula:

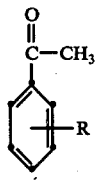   II in which R has the same meanings as in formula I, with phenylhydrazine to form a substituted acetophenone phenylhydrazone, represented by the formula:

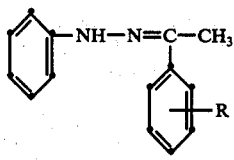   III in which R has the same meanings as in formula I and cyclising the acetophenone phenylhydrazone of formula III either with a dehydrating agent such as, for example, sulphuric acid, polyphosphoric acid or zinc chloride, or by thermolysis, to form the required 2-phenyl-indole derivative of formula I.

The derivatives corresponding to formula I may alternatively be prepared, according to the Bischler Indole Synthesis, by reacting a substituted acetophenone, represented by the formula:

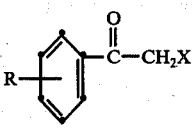   IV in which R has the same meanings as in formula I and X represents a halogen atom, preferably bromine or chlorine, with aniline to form the required 2-phenyl-indole derivative of formula I.

The derivatives corresponding to formula I, wherein R represents a radical $R_1O-$, $R_1$ representing an isopropyl, carbethoxymethyl, carbethoxyisopropyl, acetyl, docosanoyl, benzoyl, benzyl or allyl radical or a branched-or straight-chain alkyl group containing from 6 to 12 carbon atoms, may alternatively be prepared by reacting an appropriate substance of formula I, in which R represents a hydroxy radical, the said substance having been prepared by one of the two general methods described above, with a derivative represented by the formula:

$R_1-X$   V wherein $R_1$ has the hereabove meanings and X represents either a halogen atom or a hydroxy or acetoxy radical, in the presence of potassium hydroxide or sodium methylate.

The derivatives corresponding to formula I, wherein R represents a N-acetylamino or N-benzoylamino group, may alternatively be prepared by reacting an appropriate substance of formula I, in which R represents an amino group, the said substance having been prepared by one of the two general methods described above, with a derivative of the formula:

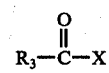   VI in which $R_3$ represents a methyl or phenyl group, X representing a halogen atom, a hydroxy radical or a

radical, $R_3$ having the meanings given above.

The derivatives corresponding to formula I, wherein R represents a mercapto group, may alternatively be prepared by demethylating an appropriate substance of formula I, in which R represents a methylmercapto radical, the said substance having been prepared by one of the two general methods described above, with sodium amide in the presence of liquid ammonia.

The derivatives corresponding to formula I, in which R represents a mercapto group, substituted by a branched-or straight-chain alkyl group containing from 2 to 12 carbon atoms or a cyclohexyl radical, may alternatively be prepared by reacting an appropriate substance of formula I, wherein R represents a mercapto group, the said substance having been prepared as indicated above, with a derivative of the formula:

$R_2-X$   VII wherein $R_2$ represents a branched-or straight-chain alkyl group containing from 2 to 12 carbon atoms or a cyclohexyl radical and X represents a halogen atom, in the presence of a sodium alcoholate such as, for example, sodium methylate.

Furthermore, 2-(4'-amino-phenyl)-indole may alternatively be prepared by the acid hydrolysis of 2-(4'-N-acetylamino-phenyl)-indole, this latter substance having been prepared by one of the two general methods given above.

Finally, 2-(4'-carboxymethoxy-phenyl)-indole may alternatively be prepared by the basic hydrolysis of 2-(4'-carbethoxymethoxy-phenyl)-indole, this latter substance having been prepared by one of the two general methods described above.

The derivatives corresponding to formula II are known substances or may be prepared by well-known procedures.

The derivatives corresponding to formula IV are known substances or may be prepared by reacting the appropriate derivative of formula II with a halogen, preferably bromine or chlorine.

The 2-phenyl-indole derivatives according to the invention have been found to be good stabilizers of polymers and co-polymers of vinyl chloride, such as, for example, polyvinyl chloride, polyvinyl chloride — polyvinyl acetate and polyvinyl chloride — polyvinylidene chloride.

They have been found to be particularly valuable as stabilizers of the polymers and co-polymers intended to be formed by extrusion-moulding, blow-moulding and calendering, mainly but not solely with a view to manufacturing containers for food and drink, such as, for example, bottles for wine, oil, vinegar and mineral water.

The substances of the invention which are listed hereunder are new and are claimed as such:
2-(4'-mercapto-phenyl)-indole (Stabilizer 1)
2-(4'-carboxy-phenyl)-indole (Stabilizer 2)
2-(4'-methylthio-phenyl)-indole (Stabilizer 3)
2-(4'-acetoxy-phenyl)-indole (Stabilizer 4)
2-(4'-carbethoxyisopropyloxy-phenyl)-indole (Stabilizer 5)
2-(4'-benzoyloxy-phenyl)-indole (Stabilizer 6)
2-(2''-ethyl-4'-hexyloxy-phenyl)-indole (Stabilizer 7)
2-(4'-dodecyloxy-phenyl)-indole (Stabilizer 8)
2-(4'-docosanoyloxy-phenyl)-indole (Stabilizer 9)
2-(4'-isopropyloxy-phenyl)-indole (Stabilizer 10)
2-(3'-amino-phenyl)-indole (Stabilizer 11)
2-(4'-carboxymethoxy-phenyl)-indole (Stabilizer 12)
2-(4'-carbethoxymethoxy-phenyl)-indole (Stabilizer 13)
2-(4'-N-acetylamino-phenyl)-indole (Stabilizer 14)
2-(4'-butylthio-phenyl)-indole (Stabilizer 15)
2-(4'-n-dodecylthio-phenyl)-indole (Stabilizer 16)
2-(4'-isopropylthio-phenyl)-indole (Stabilizer 17)
2-(4'-cyclohexylthio-phenyl)-indole (Stabilizer 18)
2-(4'-allyloxy-phenyl)-indole (Stabilizer 19)

As against this, the substances listed hereunder are already known as such but are considered as new stabilizers of polymers and co-polymers of vinyl chloride:
2-(4'-hydroxy-phenyl)-indole (Stabilizer 20)
2-(4'-benzyloxy-phenyl)-indole (Stabilizer 21)
2-(4'-amino-phenyl)-indole (Stabilizer 22)
2-(2'-amino-phenyl)-indole (Stabilizer 23)
2-(2'-N-acetylamino-phenyl)-indole (Stabilizer 24)
2-(2'-N-benzoylamino-phenyl)-indole (Stabilizer 25)
2(4'-phenyl-phenyl)-indole (Stabilizer 26)

Vinyl resins are known to deteriorate under the influence of heat and it is necessary to add a stabilizing agent to these masses of synthetic materials in order to retard thermodegradation and thus delay colouration of the resin.

Amongst the organic stabilizers used up-to-present, 2-phenyl-indole is one of the most valuable, owing to its good stabilizing power and its low toxicity. It is, in fact, widely used in the plastics industry to stabilize vinyl polymers and co-polymers, especially those which are to be used for the manufacture of containers for food and drink.

However, good stabilizing power, though necessary, is not the only quality required for a stabilizer.

The following characteristics also have great importance:
thermostability of the stabilized resin
sticking of the stabilized resin
behaviour on extrusion of the stabilized resin
behaviour on blowing of the stabilized resin
sublimation of the stabilizer
thermostability of the stabilizer itself.

Finally, as far as containers for food and drink are concerned, the extractability of the stabilizer by the food or drink contained in the recipient must be carefully evaluated.

For one or more of the above characteristics, the substances of the invention have been found to be superior to 2-phenyl-indole; especially the preferred substance, namely 2-(4'-dodecyloxy-phenyl)-indole (Stabilizer 8).

The toxicity of the substances of the invention was studied first and the satisfactory results obtained were such as to justify continuation of the investigation.

A. Acute toxicity.

The study of the acute toxicity of the stabilizers listed below was carried out by determining the dose of substance which provoked the death of 50% of the treated animals ($LD_{50}$). A gummy suspension of the substance under study was administered by oral route to groups of at least ten mice and the following results were observed:

| Stabilizers | $LD_{50}$ (mg/kg) | Toxic symptoms |
|---|---|---|
| 1 | >2000 | none |
| 3 | >3000 | none |
| 4 | >3000 | none |
| 5 | >3000 | none |
| 6 | >4000 | none |
| 7 | >2000 | none |
| 8 | >5000 | none |
| 20 | >3000 | none |
| 23 | >2000 | none |
| 2-phenyl-indole | >3000 | none |

The maximal dose which does not provoke any death ($LD_O$) was also determined by the same method and the following results were observed:

| Stabilizers | $LD_O$ (mg/kg) | Toxic symptoms |
|---|---|---|
| 15 | >3000 | none |
| 16 | >3000 | none |

B. Thermostability of the stabilized resin.

The stabilizing power of the substances of the invention was studied from two points of view:
 a. Static thermostability
 b. Dynamic thermostability These studies were performed with six different formulae of vinyl resins (hereinafter referred to as Compounds).

| Compound A | |
|---|---|
| Ingredients | Parts by weight |
| Polyvinyl chloride resin | 100 |
| Anti-shock resin | 9 |
| Epoxide soja bean oil | 2 |
| Calcium-12-hydroxy stearate | 0.2 |
| SL 2016 | 0.1 |
| Stabilizer | 0.3 |

| Compound B | |
|---|---|
| Ingredients | Parts by weight |
| Polyvinyl chloride resin | 100 |
| Anti-shock resin | 9 |
| Epoxide soja bean oil | 2 |
| Chelating agent 1832 | 0.25 |
| Solution of potassium-2-ethyl hexanoate containing 10% of potassium | 0.025 |
| Pure stearylic alcohol | 0.5 |
| Glyceryl-12-trihydroxy stearate | 0.5 |
| Glycerol trimontanate | 0.2 |
| Calcium montanate | 0.1 |
| SL 2016 | 0.1 |
| Stabilizer | 0.3 |

| Compound C | |
|---|---|
| Ingredients | Parts by weight |
| Polyvinyl chloride resin | 100 |
| Anti-shock resin | 12 |
| Epoxide soja bean oil | 3 |
| Chelating agent 1832 | 0.25 |
| Solution of potassium-2-ethyl hexanoate containing 10% of potassium | 0.025 |
| Zinc-calcium stearate | 0.2 |
| Calcium stearate | 0.2 |
| Glyceryl-12-trihydroxy stearate | 1 |
| Glycerol trimontanate | 0.3 |
| Acrylic resin | 0.5 |
| Stabilizer | 0.3 |

| Compound D | |
|---|---|
| Ingredients | Parts by weight |
| Polyvinyl chloride resin | 90 |
| Vinyl chloride - vinylidene chloride copolymer (50/50) | 10 |
| Anti-shock resin | 7 |
| Acrylic resin | 1.7 |
| Epoxide soja bean oil | 2.5 |
| 3-(2'-Phenyl-phenyl)-1,2-epoxy-propane | 0.5 |
| Calcium stearate | 0.3 |
| Zinc stearate | 0.1 |
| Glyceryl-12-trihydroxy stearate | 0.6 |
| Hydrogenated rapseed oil | 0.6 |
| Micronized silica | 0.2 |
| Antioxydant | 0.1 |
| Stabilizer | 0.15 |

| Compound E | |
|---|---|
| Ingredients | Parts by weight |
| Polyvinyl chloride resin | 90 |
| Vinyl chloride - vinylidene chloride copolymer (50/50) | 10 |
| Anti-shock resin | 7 |
| Acrylic resin | 1.7 |
| Epoxide soja bean oil | 0.5 |
| 3-(2'-phenyl-phenyl)-1,2-epoxy-propane | 0.5 |
| Organo-stannic stabilizer | 0.5 |
| Calcium stearate | 0.2 |
| Hydrogenated rapseed oil | 0.5 |
| Methyl-dihydroxy stearate | 0.2 |
| Micronized silica | 0.2 |
| Anti-oxydant | 0.1 |
| Stabilizer | 0.15 |

| Compound F | |
|---|---|
| Ingredients | Parts by weight |
| Polyvinyl chloride resin | 100 |
| Anti-shock resin | 12 |
| Epoxide soja bean oil | 3 |
| Glyceryl-12-trihydroxy stearate | 1 |
| Glycerol trimontanate | 0.3 |
| Acrylic resin | 0.5 |
| Stabilizer | 1 |

The following ingredients are defined below:

| | |
|---|---|
| SL 2016 | solution of zinc-2-ethyl-hexanoate in a mixture of hydrocarbons boiling between 158° C and 184° C. |
| Chelating agent 1832 | diphenyldecylphosphite : 67 parts by weight solution of 10% zinc octoate in diisobutylic phtalate : 33 parts by weight. |

Static thermostability:

The different compounds were mixed and calendered in a mixer of which the cylinders were heated to 160° C. The rigid sheets so obtained were then heated in an oven to a temperature between 180° C and 215° C, until incipient carbonization.

A stove with rotating drums, ventilated and equipped with a thermostat was used for this operation. In the trials described hereunder, the behaviour of a sheet containing the stabilizer to be tested was compared to that of a sheet of the same formula but containing 2-phenyl-indole as stabilizer.

Comparison can be made by one of two methods, namely:

1. The colouration of the sheets, of which samples were removed from the stove at fixed intervals was compared to a standard scale of colouration, known as the GARDNER Scale, and expressed in terms of the reference figures of the GARDNER Scale.

Comparisons were made with a GARDNER Scale Comparator which contains 18 filters of coloured glass and which offers the possibility of observing by transparency and in a limited field of view both the sheet and the reference filters.

It may happen that the colour of the sheets is far removed from that of the GARDNER Scale in which case comparison is difficult, if not impossible.

The following results were obtained:

2-(4'-Dodecyloxy-phenyl)-indole

Compound B was used and the sheets obtained presented the following characteristics:

| Initial thickness of the control sheet | 0.9 mm |
| Initial thickness of the test sheet | 1.15 mm |
| Temperature of the stove | 210° C. |

| | TIME IN MINUTES | | | | | | | |
|---|---|---|---|---|---|---|---|---|
| STABILIZERS | 0 | 3 | 6 | 9 | 12 | 15 | 18 | 21 |
| 2-phenyl-indole | 1 | 1 | 2 | 3 | 4 | 6 | 8 | >18 |
| 8 | 1 | 1 | 2 | 3 | 3 | 5 | 7 | 11 |

After 24 minutes, the control and test sheets are burnt. However at 21 minutes, Stabilizer 8 is clearly superior to 2-phenyl-indole.

It should be emphasized that after 21 minutes, the thickness of the control sheet was 0.9 mm whereas that of the test sheet was 1.30 mm, which further indicates that Stabilizer 8 is superior to 2-phenyl-indole.

2-(4'-Isopropylthio-phenyl)-indole

Compound A was used.

| Initial thickness of the control sheet | 0.95 mm |
| Initial thickness of the test sheet | 1.1 mm |
| Temperature | 185° C |

| | TIME IN MINUTES | | | | | | | | |
|---|---|---|---|---|---|---|---|---|---|
| STABILIZERS | 0 | 6 | 12 | 18 | 24 | 30 | 36 | 42 | 48 | 54 |
| 2-phenyl-indole | 1 | 1 | 3 | 5 | 11 | 12 | 14 | 14 | 14 | burnt |
| 17 | 1 | 1 | 2 | 4 | 9 | 11 | 12 | 13 | 14 | burnt |

2. It is also possible to use a simplified method which is more rapid and with which valid results are also obtained: a reference scale is drawn up with sheets of thermally treated polyvinyl chloride, of which the colourations have been definitely determined in GARDNER degrees as above. A GARDNER subscale is thus obtained in polyvinyl chloride sheets which can be directly compared to the sheets to be tested without using the comparator.

The following results were obtained with the said simplified method:

2-(4'-Mercapto-phenyl)-indole

Compound A was used.
Temperature: 210° C

| STABILIZERS | TIME IN MINUTES | | | | | |
|---|---|---|---|---|---|---|
| | 0 | 3 | 6 | 9 | 12 | 15 |
| 2-phenyl-indole | 1 | 2 | 2.5 | 7 | 11 | 13 |
| 1 | 1 | 2 | 2.5 | 7 | 11 | 12 |

At 15 minutes, the control sheet was burnt along its edges whereas the test sheet was not, thus showing the superiority of Stabilizer 1 over 2-phenyl-indole. It should be noted that the colour of the control sheet was difficult to appreciate because it presented a pink reflection.

2-(4'-Methylthio-phenyl)-indole

Compound A was used.
Temperature: 210° C

| STABILIZERS | TIME IN MINUTES | | | | | |
|---|---|---|---|---|---|---|
| | 0 | 3 | 6 | 9 | 12 | 15 |
| 2-phenyl-inodle | 1 | 2 | 3 | 8 | 11 | 12 |
| 3 | 1 | 1 | 2 | 3 | 8 | 10 |

At 15 minutes, the control sheet was badly burnt whereas the test sheet was not, which proves that Stabilizer 3 is markedly superior to 2-phenyl-indole.

2-(4'-Carbethoxyisopropyloxy-phenyl)-indole

Compound A was used.
Temperature: 210° C

| STABILIZERS | TIME IN MINUTES | | | | | |
|---|---|---|---|---|---|---|
| | 0 | 3 | 6 | 9 | 12 | 15 |
| 2-phenyl-indole | 1 | 2 | 2 | 3 | 10 | 12 |
| 5 | 1 | 1 | 1 | 2 | 10 | 11 |

At 15 minutes, the control sheet was burnt along its edges, whereas the test sheet was not. Stabilizer 5 thus showed itself to be markedly superior to 2-phenyl-indole.

2-(2''-Ethyl-4'-hexyloxy-phenyl)-indole

Compound D was used.
Temperature: 185° C

| STABILIZERS | TIME IN MINUTES | | | |
|---|---|---|---|---|
| | 0 | 10 | 20 | 30 |
| 2-phenyl-indole | 1 | 2 | >2 | 3 |
| 7 | <1 | <2 | 2 | <3 |

Stabilizer 7 showed itself to be markedly superior to 2-phenyl-indole, principally with respect to the colouration given to the co-polymer, which was less yellow with Stabilizer 7 than with 2-phenyl-indole. This is important with regard to certain uses.

2-(2''-Ethyl-4'-hexyloxy-phenyl)-indole

Compound E was used.
Temperature: 185° C

| STABILIZERS | TIME IN MINUTES | | | |
|---|---|---|---|---|
| | 0 | 10 | 20 | 30 |
| 2-phenyl-indole | <1 | 1 | 2 | 3 |
| 7 | <1 | <1 | <2 | <3 |

The same comments as hereabove apply.

2-(4'-Dodecyloxy-phenyl)-indole

Compound C was used.
Temperature: 210° C

| STABILIZERS | TIME IN MINUTES | | | | | | | |
|---|---|---|---|---|---|---|---|---|
| | 0 | 10 | 20 | 30 | 40 | 50 | 55 | 60 |
| 2-phenyl-indole | 1 | 1.5 | 2 | <3 | 3 | >3 | 3.5 | >4 |
| 8 | 1 | 1.5 | 2 | 2.5 | <3 | 3 | 3 | 3.5 |

The colourations are fairly far removed from the GARDNER Scale and the intensity of the colour is therefore difficult to appreciate. However, it can be seen that after 60 minutes Stabilizer 8 is superior as a stabilizer to 2-phenyl-indole.

2-(4'-Dodecyloxy-phenyl)-indole

Compound D was used.
Temperature: 185° C

| STABILIZERS | TIME IN MINUTES | | | |
|---|---|---|---|---|
| | 0 | 10 | 20 | 30 |
| 2-phenyl-indole | 1 | 2 | >2 | 3 |
| 8 | <1 | <2 | 2 | <3 |

In this case, Stabilizer 8 was superior to 2-phenyl-indole, principally with respect to the colouration given to the co-polymer during the first 30 minutes. The co-polymer containing Stabilizer 8 was in fact less yellow-coloured than that containing 2-phenyl-indole.

2-(4'-Dodecyloxy-phenyl)-indole

Compound E was used.
Temperature: 185° C

| STABILIZERS | TIME IN MINUTES | | | |
|---|---|---|---|---|
| | 0 | 10 | 20 | 30 |
| 2-phenyl-indole | <1 | 1 | 2 | 3 |
| 8 | <1 | <1 | <2 | <3 |

The same comments as hereabove apply.

2-(3'-Amino-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 13 | burnt |
| 11 | 3 | 3 | 4 | 5 | 10 | 12 | burnt |

Examination of the colourations at 0 and 3 minutes showed that Stabilizer 11 gave to the polymer a relatively intense yellow colouration, but this colouration developed less rapidly than that due to 2-phenyl-indole.

2-(4'-Carboxymethoxy-phenyl)-indole

Compound A was used.
Temperature: 210° C

| STABI-LIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 13 | burnt |
| 12 | 2 | 2 | 3 | yellow/green | yellow/green | brown | burnt |

The colourations of the polymer containing Stabilizer 12 after 9, 12 and 15 minutes were far removed from the colourations of the GARDNER Scale and it was impossible to determine them in GARDNER degrees.

However, it was clear that the colourations due to Stabilizer 12 developed less rapidly than those due to 2-phenyl-indole.

2-(4'-Carbethoxymethoxy-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 13 | burnt |
| 13 | 2 | 2 | 3 | 3 | 9 | 11 | burnt |

Stabilizer 13 was markedly superior to 2-phenyl-indole.

2-(4'-N-Acetylamino-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 13 | burnt |
| 14 | 2 | 2 | 3 | 4 | 8 | 12 | burnt |

Stabilizer 14 was slightly superior to 2-phenyl-indole.

2-(4'-Hydroxy-phenyl)-indole

Compound A was used.
Temperature: 210° C

| STABILIZERS | TIME IN MINUTES | | | | | |
|---|---|---|---|---|---|---|
| | 0 | 3 | 6 | 9 | 12 | 15 |
| 2-phenyl-indole | 1 | 1 | 3 | 10 | 11 | 13 |
| 20 | 1 | 1 | 2 | 4 | 9 | 11 |

Stabilizer 20 was markedly superior to 2-phenyl-indole.

2-(4'-amino-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 13 | burnt |
| 22 | 2 | 3 | 3 | 4 | 6 | 12 | burnt |

Examination of the colourations at 0 and 3 minutes showed that Stabilizer 22 gave to the polymer a relatively strong yellow colouration, but this colouration developed less rapidly than that due to 2-phenyl-indole.

2-(2'-Amino-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 14 | burnt |
| 23 | pink | pink | pink | 4 | 6 | 12 | partially burnt |

Although it was impossible to determine in GARDNER degrees the colourations of the sheet containing Stabilizer 23, it appeared nevertheless that Stabilizer 23 was superior to 2-phenyl-indole.

2-(2'-N-Benzoylamino-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 10 | 14 | burnt |
| 25 | 2 | 2 | 4 | 6 | 9 | 12 | burnt |

Stabilizer 25 was slightly superior to 2-phenyl-indole.

2-(4'-Phenyl-phenyl)-indole

Compound A was used.
Temperature: 210° C

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 1 | 2 | 5 | 9 | 13 | burnt |
| 26 | 2 | 2 | 3 | 4 | 5 | 12 | 14 |

Stabilizer 26 was markedly superior to 2-phenyl-indole.

Finally, trials were carried out with Stabilizers 15, 16 and 17 and with 2-phenyl-indole. Compound A was used and the temperature was 210° C.

The following results were obtained:

| STABILIZERS | TIME IN MINUTES | | | | | | |
|---|---|---|---|---|---|---|---|
| | 0 | 3 | 6 | 9 | 12 | 15 | 18 |
| 2-phenyl-indole | 1 | 2 | 3 | 9 | 11 | 13 | burnt |
| 15 | 1 | 1 | 2 | 5 | 10 | 13 | burnt |
| 16 | 1 | 1 | 2 | 5 | 10 | 13 | burnt |
| 17 | 1 | 1 | 2 | 4 | 10 | 13 | burnt |

Stabilizers 15, 16 and 17 were very rapidly found to be superior to 2-phenyl-indole.

b. Dynamic thermostability:

The dynamic thermostability of resins containing respectively 2-(4'-dodecyloxy-phenyl)-indole and 2-phenyl-indole as stabilizers was compared by using the Compounds numbered hereunder:

No. 609: Compound C with 2-phenyl-indole as Stabilizer
No. 675: Compound C with Stabilizer 8
No. 633: Compound F with 2-phenyl-indole as Stabilizer
No. 673: Compound F with Stabilizer 8

The tests were performed on a plastograph, working at a temperature of 190° C, turning at a speed of 60 r.p.m. and containing a charge of 30 g of gelled material.

Two curves were drawn namely:

a decomposition curve giving the value of the resistant torque (m kg) in relation to time.

From this curve, two important results were obtained: the minimal resistant torque and the time of decomposition.

a curve giving the self-heating time in relation to temperature.

The self-heating time is defined by the moment when the temperature of the sheet exceeds the temperature of the plastograph (190° C).

The results given in the following Table were obtained from these curves:

| Measurements | Compounds Nos. | | | |
|---|---|---|---|---|
| | 609 | 675 | 633 | 673 |
| Minimal resistant torque in m kg | 1.1 | 1.09 | 0.96 | 1.015 |
| Decomposition time in min. | 23.5 | 22.5 | 43.5 | 42.5 |
| Self-heating time in min. | 6 | 6 | 9 | 12 |

The measurements are comparable, although Stabilizer 8 showed a slight superiority over 2-phenyl-indole.

C. Sticking of the stabilized material.

Compounds Nos. 609 and 675 were placed in a mixer of the type previously used for studying static thermostability with cylinders at a fixed temperature of 210° C.

They were submitted to alternate periods of 3 minutes of mixing and 3 minutes of rest.

The results which were obtained with Stabilizer 8 and 2-phenyl-indole are comparable.

D. Behaviour on extrusion of the stabilized material.

Compounds Nos. 609 and 675 were extruded with an extruder fitted with a screw having a diameter of 45 mm. The results are comparable.

E. Behaviour on blowing.

Bottles were moulded with Compounds Nos. 609, 675, 633 and 673 and it was observed that the behaviour on blowing was similar for the four resins.

F. Sublimation of the stabilizers of the invention.

It is well-known that 2-phenyl-indole presents the disadvantage of sublimating when being handled in the form of powder, during the formation of the compound and during the extrusion of the latter. This relatively extensive sublimation constitutes a major disadvantage because, in addition to the not inconsiderable loss of stabilizer, it causes pollution of the atmosphere in the workshops where the various operations are carried out. The tendency to sublimate of 2-(4'-dodecyloxyphenyl)-indole (Stabilizer 8) was compared to that of 2-phenyl-indole.

A sample of the substance to be tested was introduced into a test tube and heated under reduced pressure. The fraction of sublimated substance was recovered on a mobile cold wall.

After a certain period of time, the sublimated substance was weighed and the result expressed as a percentage of the weight of the starting-material.

The results obtained can only be of relative value, enabling a comparison to be made between two products tested under the same conditions.

| Operating conditions (chosen at random). | |
|---|---|
| Temperature of heating | 120° C |
| Temperature of the cold wall | 13° C |
| Pressure | 15 Torr |
| Duration of heating | 150 minutes |
| Starting-weight | 150 mg |

The percentages of sublimated substance were respectively:

2-phenyl-indole: 26.9%

Stabilizer 8: 0.6%

The ratio between the percentages of sublimation of Stabilizer 8 and of 2-phenyl-indole shows that the sublimation of Stabilizer 8 is forty times less than that of 2-phenyl-indole.

G. Thermostability of the stabilizers.

The thermostability of Stabilizer 8 and that of 2-phenyl-indole were studied by differential thermoanalysis and by thermogravimetric analysis.

a. Differential thermoanalysis:

Differential thermoanalysis diagrams were drawn up by studying 2 mg samples of material placed in a non-airtight container, the rate of temperature increase being 2° C/minute and sensitivity 4 mcal/sec.

Diagrams were made out for 2-phenyl-indole (i) and Compound 8 (ii) and enabled the following conclusions to be drawn:

i.

2-Phenyl-indole sublimates at 140° C and particularly from 185°–190° C (melting point).

There is no loss of water at 100° C. Decomposition appears to start at about 210°–220° C.

It is very difficult to determine the decomposition temperature with accuracy because it is not possible to separate the effect of thermolysis from that of sublimation.

ii.

There is a loss of water between 100° and 114° C, melting occurs at 203° C and decomposition starts at 300° C followed by a series of exothermic waves.

b. Thermogravimetric analysis

This analysis necessitated two series of trials carried out under air and under inert gas (Argon) in order to eliminate any possible effect of oxygen. The results obtained were identical.

The temperature increase rate was 80° C/hour. Thermograms were drawn up under air for both 2-phenyl-indole (i) and for Stabilizer 8 (ii) and enabled the following conclusion to be drawn:

i.

Weight loss starts at about 190°–195° C. It is due to both sublimation and to incipient decomposition.

In the case of the trial carried out under air, a yellowish residue was, in fact, obtained at 210° C which constitutes proof of decomposition. Although the sample was not kept at 210° C, it can be safely assumed that had this temperature been maintained for a prolonged period of time, at least in the presence of air, the sample would have undergone extensive degradation.

ii.

Loss of weight begins at about 295° C, which corresponds to the beginning of decomposition.

The results of the thermogravimetric analysis confirm the results of the differential thermoanalysis, thus showing that Stabilizer 8 has greater thermostability than 2-phenyl-indole.

This fact is very important since the preparation and processing of the resin often involve temperatures ranging from 180° C to 220° C, in some cases for several minutes.

H. Extractibility of the stabilizers.

The stabilizers according to the invention may be used to stabilize polymers which are intended for the manufacture of packaging and containers for food and drink and it was therefore necessary, in spite of their low toxicity, to determine their extractibility by solvents simulating food and drink.

This study was carried out in accordance with the requirements of the Food and Drug Administration (U.S.A.).

The extractions were performed in semi-rigid bottles, prepared with Compounds Nos. 609 and 675, and with the following solvents: water, an aqueous solution of acetic acid (3%), ethanol-water 50/50, heptane.

The bottles had the following specifications:

| | |
|---|---|
| Diameter | 62 mm |
| Height | 170 mm |
| Capacity | 375 ml |
| Weight | 28 g |

The ratio of the volume of solvent to the surface of plastic material exposed to extraction was about 1 cm² to 100 ml of solvent, taking into account the geometric characteristics of the bottles.

OPERATING CONDITIONS

| | |
|---|---|
| Temperature | 49° C |
| Heating | a thermostated oven for the non-inflammable solvents (water and acetic acid) a thermostated water-bath for the inflammable solvents (alcohol and heptane) |
| Duration of extraction | these are indicated under each result. They are intentionally longer than those which would have given stable maximum values. |

The quantity of stabilizer extracted was determined by colorimetric assay using p-dimethylaminobenzaldehyde, in accordance with the method described in Analytical Chemistry 36, 425–26 (1964).

A blank trial was carried out with a compound of the same formula as Compounds Nos. 609 and 675, but without any stabilizer. A purely negative result was obtained. All the results are given in the Table hereunder.

The amounts of stabilizer assayed are expressed in μg per liter of extraction solvent or, which is the same, per 1000 cm² of surface submitted to extraction.

| Solvents | Compounds Nos. | |
|---|---|---|
| | 609 | 675 |
| Water | 40 (6 days) | <3 (10 days) |
| 3% Aqueous solution of acetic acid | <3 (20 days) | <3 (20 days) |
| Aqueous ethanol 50/50 | 100 (9 days) | <10 (9 days) |
| Heptane | 875 (48 hours) | 175 (48 hours) |

The same trials were carried out with Compound A containing 2-(4'-dodecylthio-phenyl)-indole (Stabilizer 16) as stabilizer and the following results were obtained:

| | |
|---|---|
| Water | <3 (10 days) |
| 3% Aqueous solution of acetic acid | <3 (20 days) |
| Aqueous ethanol 50/50 | <10 (9 days) |
| Heptane | 175 (48 hours). |

These results show that Stabilizers 8 and 16 are markedly less extractible than 2-phenyl-indole with regard to water, aqueous ethanol and heptane.

In the case of diluted acetic acid, the amounts extracted are approximately the same but it is difficult to draw a conclusion because these amounts are below the sensitivity threshold of the method of assay.

With particular regard to water, it is clear that Stabilizers 8 and 16 are markedly superior to 2-phenyl-indole since their extractibility is at least 10 times less than that of the latter. This finding is important because it is closely related to the problem of providing containers for mineral waters and the possible pollution of the latter by the recipient in stabilized polymer.

The stabilizers covered by the invention are introduced into the thermoplastic material in the proportion of 0.1% to 1% by weight.

The following Examples provide a non-limitative illustration of the processes of preparation of the substances covered by the invention:

EXAMPLE 1

2-(4'-Dodecyloxy-phenyl)-indole

To 300 ml of 78% sulphuric acid heated to 45°–50° C, were added 304 g (1 mol) of 4-dodecyloxy-acetophenone and, drop-by-drop, 98 ml (1 mol) of phenylhydrazine, the reaction medium being continuously stirred. The temperature was allowed to reach 70°–75° C, after which the mixture was heated to 100° C for 15 minutes. The reaction medium was then poured into iced-water and extracted with ether. The organic phase was dried over anhydrous sodium sulphate, discoloured and concentrated.

After recrystallization from toluene, 72 g of 2-(4'-dodecloxy-phenyl)-indole were obtained.

M.P.: 201° C

Yield: 20%

EXAMPLE 2

2-(4'-Hydroxy-phenyl)-indole a. Preparation of 4-hydroxy-acetophenone-phenylhydrazone.

A mixture of 40.8 g (0.3 mol) of 4-hydroxy-acetophenone, 33 ml (0.3 mol) of phenylhydrazine, 100 ml of ethanol and 1.5 ml of acetic acid was refluxed under nitrogen for 10 hours.

The mixture was evaporated to dryness and the residue was recrystallized from toluene to give 43.4 g of crude product. By concentrating the mother-liquors a further 20.6 g of substance was recovered which was added to the 43.4 g of crystals already obtained. The 64 g of crude 4-hydroxy-acetophenone-phenylhydrazine so obtained was directly engaged in the following step.

By the above procedure but using the appropriate starting-products, the following compounds were prepared:

4-methylthio-acetophenone-phenylhydrazone
4-mercapto-acetophenone-phenylhydrazone b. Preparation of 2-(4'-hydroxy-phenyl)-indole.

While stirring 56.5 g (0.25 mol) of 4-hydroxy-acetophenone-phenyl-hydrazone were added in small portions to 450 g of polyphosphoric acid (a mixture of orthophosphoric acid — phosphoric anhydride 40/50) previously heated to 150° C. The mixture was heated to 180° C for 10 minutes and then allowed to stand at room-temperature for 10 minutes. One liter of water was added to the mixture and the reaction medium was stirred until disappearance of the oily phase.

The reaction medium was cooled to room-temperature and the aqueous suspension was extracted several times with ether. The collected ethereal phases were washed with water and dried over anhydrous sodium sulphate.

After filtration through a neutral alumina column and recrystallization from toluene, 26.8 g of 2-(4'-hydroxy-phenyl)-indole were obtained.

M.P.: 235° C
Yield: 51%

By the procedure described above but using the appropriate starting-products, the compounds given hereunder were prepared:

| Compounds | Melting Point |
|---|---|
| 2-(4'-methylthio-phenyl)-indole | 225° C (toluene) |
| 2-(4'-mercapto-phenyl)-indole | 210° C (toluene) |

EXAMPLE 3

2-(4'-Carboxy-phenyl)-indole a. Preparation of 4-cyano-acetophenone-phenylhydrazone.

A mixture of 7.4 g (0.05 mol) of 4-cyano-acetophenone, 5.6. g (0.05 mol) of phenylhydrazine, 60 ml of ethanol and 3 drops of acetic acid was refluxed for 3 hours. The mixture was allowed to stand for 30 minutes and the precipitate so obtained was centrifuged out, washed with 100 ml of hexane and dried to give 10.3 g of 4-cyano-acetophenone-phenylhydrazone.

M.P.: 164° C
Yield: 91% b. Preparation of 2-(4'-cyano-phenyl)-indole.

A mixture of 10 g (0.045 mol) of 4-cyano-acetophenone-phenylhydrazone and 50 g of anhydrous zinc chloride was heated to a temperature of 220° C for 10 minutes and then allowed to stand for 30 minutes. A black resin was obtained and treated with 100 ml of ethyl acetate. The solution was filtered and 100 ml of toluene were added to the filtrate to give a solution which was chromatographed on a neutral alumina column, with a mixture of toluene - ethyl acetate (50/50) as eluant. After recrystallization from methanol, 2.4 g of 2-(4'-cyano-phenyl)-indole were obtained.

M.P.: 201.2° C
Yield: 30% c. Preparation of 2-(4'-carboxy-phenyl)-indole.

A mixture of 2 g (0.009 mol) of 2-(4'-cyano-phenyl)-indole, 50 ml of ethanol and 3 drops of concentrated sulphuric acid was refluxed for 2 hours to give 2-(4'-carboxamido-phenyl)-indole.

A mixture of 4.72 g (0.02 mol) of 2-(4'-carboxamido-phenyl)-indole, 10 g of potassium hydroxide and 50 ml of ethanol was refluxed for 24 hours, after which the alcohol was evaporated off under vacuum.

The residue was taken up in 100 ml of water and extracted with 100 ml of ethyl acetate. The aqueous phase was filtered and the filtrate was acidified with concentrated hydrochloric acid until the formation of a white precipitate. After a second extraction with ethyl acetate and concentration of the solvent, the residue was chromatographed on a silica gel column, with diethyl ether as eluant.

After recrystallization from aqueous acetone, 3.2 g of 2-(4'-carboxy-phenyl)-indole were obtained.

M.P.: 204.6° C
Yield: 67%

EXAMPLE 4

2-(3'-Amino-phenyl)-indole 43.2 g (0.4 mol) of phenylhydrazine were slowly added to 240 g of 98% sulphuric acid, the temperature being maintained at 25° C, then 54 g (0.4 mol) of 3-amino-acetophenone were added in 10 minutes and the mixture was heated to 85° C. The temperature of the mixture was allowed to reach 90° C and this latter temperature was maintained for 15 minutes. The reaction medium was allowed to cool to room-temperature and was then poured into 2 liters of iced-water. The precipitate was filtered out, washed with 500 ml of a diluted ammoniacal solution and dried.

The crude product was recrystallized from a mixture of toluene — ethanol (1/1) and was chromatographed on an alumina column, with ether as eluant.

After further recyrystallization from a mixture of ether — heptane, 16.6 g of 2-(3'-amino-phenyl)-indole were obtained.

M.P.: 166° C
Yield: 20%

EXAMPLE 5

2-(2'-Amino-phenyl)-indole.

a. Preparation of 2-amino-acetophenone-phenylhydrazone.

A mixture of 13.5 g (0.1 mol) of 2-amino-acetophenone, 10.8 g (0.1 mol) of phenylhydrazine, 20 ml of ethanol and 1 ml of acetic acid was refluxed for 7 hours. The mixture was allowed to stand at room-temperature for 1 hour and then at 5° C for 30 minutes.

The precipitate was centrifuged out and transferred into 100 ml of hexane. The suspension was stirred for one hour and filtered. The crystals were dried and the mother-liquors were concentrated and filtered. Finally 20.5 g of 2-amino-acetophenone-phenylhydrazone were obtained.

M.P.: 106°–108° C
Yield: 91% b. Preparation of 2-(2'-amino-phenyl)-indole.

An intimate mixture of 10 g (0.045 mol) of 2-amino-acetophenone-phenylhydrazone and 50 g of zinc chloride was heated to about 165° C. After a few minutes a homogeneous brownish liquid was obtained and was mixed and heated for 10 minutes.

After standing for 30 minutes at room-temperature, the mixture was taken up with 10% hydrochloric acid and stirred until complete dissolution of the zinc chloride. The yellow suspension obtained was filtered and the crystals were washed with a minimum of cold water and then poured into 100 ml of 10% hydrochloric acid. The reaction medium was heated until a homogenous solution was obtained, after which the solution was filtered. The filtrate was cooled and taken up in ammonia hydrate until precipitation of a whitish substance.

The reaction medium was centrifuged and the precipitate was washed several times with cold water. Purification was carried out twice and after two recrystallizations from toluene, 7.5 g of 2-(2'-amino-phenyl)-indole were obtained.

M.P.: 156° C
Yield: 76%

EXAMPLE 6

2-(4'-Phenyl-phenyl)-indole a. Preparation of 4-phenyl-acetophenone-phenylhydrazone.

A solution of 1000 ml of toluene containing 196 g (1 mol) of 4-phenyl-acetophenone, 162 g (1.5 mol) of phenylhydrazine and 5 ml of acetic anhydride was refluxed for 1 hour. After cooling, a precipitate of 4-phenyl-acetophenone-phenylhydrazone was obtained and directly engaged in the following step.

b. Preparation of 2-(4'-phenyl-phenyl)-indole.

A mixture of orthophosphoric acid/phosphoric anhydride (35/45) was heated to 150° C and 286 g (1 mol) of 4-phenyl-acetophenone-phenylhydrazone were added to the mixture, the temperature being maintained at 170° C for 30 minutes. The reaction medium was cooled to 80° C and, while stirring, was poured into 2 liters of water. The precipitate which was obtained was washed with water until neutrality, dried and recrystallized from N,N-dimethylformamide and then washed with hot ethanol to give 95 g of 2-(4'-phenyl-phenyl)-indole.

M.P.: 301° C
Yield: 35%

EXAMPLE 7

2-(4'-N-Acetylamino-phenyl)-indole a. Preparation of 4-acetamido-acetophenone-phenylhydrazone.

A mixture of 5.9 g (0.033 mol) of 4-acetamido-acetophenone, 4 ml (0.033 mol) of phenylhydrazine, 50 ml of ethanol and a catalytic quantity of acetic acid was refluxed for 3 hours and then allowed to stand at room-temperature for 1 hour. The crystals which formed were centrifuged out, washed with 50 ml of hexane and then directly engaged in the following step.

b. Preparation of 2-(4'-N-acetylamino-phenyl)-indole.

A mixture of 5.34 g (0.02 mol) of 4-acetamido-acetophenone-phenylhydrazone and 25 g of anhydrous zinc chloride was heated to 220° C for 1 hour and was then allowed to stand at room-temperature for 30 minutes.

A hard resin was obtained and was taken up in 500 ml of 10% hydrochloric acid. The mixture was vigorously stirred until the resin was dissolved and a flocculent solution obtained. The solution was centrigued and washed with 100 ml of water. The crude substance was chromatographed on a silica gel column with methyl-ethylketone as eluant to give, after recrystallization from aqueous acetone, 3.5 g of 2-(4'-N-acetylamino-phenyl)-indole.

M.P.: 292° C
Yield: 70%

EXAMPLE 8

2-(4'-Dodecyloxy-phenyl)-indole

To 32.5 g (0.35 mol) of boiling aniline were added in 15 minutes 33.85 g (0.1 mol) of molten ω-chloroparadodecyloxy-acetophenone, the temperature of the reaction medium being maintained at 180° C for 20 minutes after the end of the operation of addition.

The mixture was poured into a diluted solution of hydrochloric acid and was extracted with benzene. The organic phase was washed with water, dried and concentrated at reduced pressure. The crude substance was wetted with a mixture of toluene-heptane, then filtered and dried to give 22.6 g of 2-(4'-dodecyloxy-phenyl)-indole.

M.P.: 204° C
Yield: 60%.

EXAMPLE 9

2-(4'-Phenyl-phenyl)-indole

A mixture of 372 g (4 mols) of aniline and 230 g (1 mol) of ω-chloroparaphenyl-acetophenone was refluxed for 105 minutes. After cooling to about 50°–80° C, the mixture was poured into iced-water containing 50 ml of concentrated hydrochloric acid to give a precipitate which was filtered out, washed with water, dried and then recrystallized from N,N-dimethylformamide. The pure substance was then filtered out and washed with ethanol to give 67.2 g of 2-(4'-phenyl-phenyl)-indole.

M.P.: 302° C
Yield: 25%

EXAMPLE 10

2-(4'-Dodecyloxy-phenyl)-indole

To a suspension of 67.5 g (1.25 mol) of sodium methylate in 1200 ml of N,N-dimethylformamide was added under nitrogen a solution of N,N-dimethylformamide containing 209 g (1 mol) of 2-(4'-hydroxy-phenyl)-indole, prepared as in Example 2. The mixture was stirred for 25 minutes, was then heated to 90° C, 256 g (1.25 mol) of 1-chloro-dodecane were added, drop-by-drop and the solution was refluxed for 10 hours.

After cooling, the substance which was obtained was filtered out and washed with water.

The precipitate was dried and recrystallized twice from N,N-dimethylformamide and once from benzene to give 268 g of 2-(4'-dodecyloxyphenyl)-indole.

M.P.: 204° C
Yield: 71%

By the above procedure but using the appropriate starting-products, the following compounds were prepared:

| Compounds | Melting Point |
| --- | --- |
| 2-[4'-(2''-ethyl-hexyloxy)-phenyl]-indole | 191° C |
| 2-(4'-carbethoxymethoxy-phenyl)-indole | 216° C |
| 2-(4'-isopropyloxy-phenyl)-indole | 196° C |

EXAMPLE 11

2-(4'-Carboxymethoxy-phenyl)-indole

To 350 ml of a 1 N hydroethanolic solution of soda were added 29.5 g (0.1 mol) of 2-(4'-carbethoxymethoxy-phenyl)-indole, prepared as in Example 10 and the solution was stirred and refluxed for 3 hours. The excess of soda was neutralized with 3 N sulphuric acid and the alcohol was distilled off. The residue was taken up in water and the aqueous solution was refluxed for 20 minutes in the presence of active charcoal.

The solution was filtered and the filtrate was acidified by 3 N sulphuric acid. The solution was then centrifuged, washed until disappearance of the sulphate ions and then dried to give 13.3 g of 2-(4'-carboxymethoxy-phenyl)-indole.

M.P.: 243° C

Yield: 50%

EXAMPLE 12

2-(4'-Carbethoxyisopropyloxy-phenyl)-indole

To a solution of sodium ethylate were added 16.72 g (0.08 mol) of 2-(4'-hydroxy-phenyl)-indole, prepared as in Example 2, and the solution was stirred under nitrogen and at room-temperature for one hour.

The solution was evaporated to dryness under vacuum and the residue was taken up in 100 ml of dry acetone. While still under nitrogen vapour 18 g (0.1 mol) of ethyl bromoisobutyrate were added, drop-by-drop, and the reaction medium was refluxed for 48 hours. The substance which precipitated was filtered out and washed with dry acetone. The filtrate was concentrated under vacuum and the residue taken up in toluene and then filtered through a silica gel column, with toluene as eluant. After having eliminated the solvent a colourless paste, which crystallized when poured into cyclohexane was obtained. After recrystallization from cyclohexane 15 g of 2-(4'-carbethoxyisopropyloxy-phenyl)-indole were obtained.

M.P.: 106.9° C

Yield: 58%

EXAMPLE 13

2-(4'-Benzyloxy-phenyl)-indole

While stirring and under nitrogen, a mixture of 3.14 g (0.15 mol) of 2-(4'-hydroxy-phenyl)-indole, prepared as in Example 2, 2.1 g of anhydrous potassium carbonate and 100 ml of anhydrous acetone was refluxed and a solution of 50 ml of anhydrous acetone containing 1.8 ml (0.015 mol) of benzyl bromide was then added, drop-by-drop. The solution was heated for 4 hours and 0.4 ml (0.003 mole) of benzyl bromide was added with 0.5 g of potassium carbonate. Heating was continued for 4 hours and the hot solution was filtered. The filter was washed with 50 ml of acetone, the filtrate was concentrated under vacuum and was taken up in 100 ml of boiling methylethylketone. The hot reaction medium was filtered and the filtrate was cooled in an ice-bath for 30 minutes. The precipitate which was obtained was centrifuged and recrystallized from methylethylketone to give 3.3 g of 2-(4'-benzyloxy-phenyl)-indole.

M.P.: 251° C

Yield: 73.5%

EXAMPLE 14

2-(4'-Acetoxy-phenyl)-indole

A mixture of 50 ml (0.5 mol) of acetic anhydride and 5.23 g (0.04 mol) of 2-(4'-hydroxy-phenyl)-indole, prepared as in Example 2, was heated on a water-bath until a homogeneous solution was obtained, which was allowed to stand at room-temperature for 1 hour. The precipitate which formed was taken up in 200 ml of iced-water, the solution was centrifuged and washed twice with 100 ml of cold water. After chromatography on a silica gel column, with dichlorethane as eluant, 5 g of crude product were obtained, which were recrystallized from ethanol to give 4.8 g of 2-(4'-acetoxy-phenyl)-indole.

M.P.: 203.2° C

Yield: 76%

EXAMPLE 15

2-(4'-Benzoyloxy-phenyl)-indole

While stirring, 500 ml of an aqueous solution containing 120 g of sodium hydroxide was added to 800 ml of a solution of tetrahydrofuran containing 209 g (1 mol) of 2-(4'-hydroxy-phenyl)-indole, prepared as in Example 2. Stirring was continued for 30 minutes and 422 g (3 mols) of benzoyl chloride were added, drop-by-drop, to the solution.

The temperature was maintained at 50° C and stirring was continued for 1 hour after the end of the operation of addition. The solvent was eliminated and the filtrate was filtered out. After recrystallization from acetone, 206 g of 2-(4'-benzoyloxy-phenyl)-indole were obtained, melting at 220° C, then at 234° C, thus showing the presence of allotropic varieties.

Yield: 66%

By the same procedure but using the appropriate starting-products, the following compound was prepared:

| Compound | Melting Point |
|---|---|
| 2-(4'-docosanoyloxy-phenyl)-indole | 140° C (N,N-dimethylformamide) |

EXAMPLE 16

2-(4'-Amino-phenyl)-indole

A suspension of 5 g (0.02 mol) of 2-(4'-N-acetylamino-phenyl)-indole, prepared as in Example 7, in 250 ml of 40% hydrochloric acid and 10 ml of absolute ethanol was refluxed for 1 hour and filtered while hot. The filtrate was allowed to stand at room-temperature for 1 hour and was then treated with concentrated ammonia until a whitish precipitate was obtained. The precipitate was centrifuged out and washed several times with cold water. After chromatography on a silica gel column, with dichlorethane as eluant, and recrystallization from toluene, 2.5 g of 2-(4'-amino-phenyl)-indole were obtained.

M.P.: 213.9° C

Yield: 61%

EXAMPLE 17

2-(2'-N-Acetylamino-phenyl)-indole 8 ml of acetic anhydride were added in one operation to 4.16 g (0.02 mol) of 2-(2'-amino-phenyl)-indole, prepared as in Example 5, and the mixture was triturated and heated until a clear homogeneous solution was obtained. The solution was allowed to stand at room-temperature for about 1 hour and to the mass thus formed 100 ml of cold water were added and the precipitate was centrifuged out and washed with 50 ml of water.

After recrystallization from aqueous ethanol, 4 g of 2-(2'-N-acetylamino-phenyl)-indole were obtained.

M.P.: 157° C

Yield: 80%

EXAMPLE 18

2-(2'-N-Benzoylamino-phenyl)-indole 2.4 ml of benzoyl chloride were added in one operation to a solution of 8 ml of dry pyridine containing 4.16 g (0.02 mol) of 2-(2'-aminophenyl)-indole, prepared as in Example 5. The precipitate was centrifuged out, washed several times with cold water and recrystallized from aqueous ethanol to give 4.5 g of 2-(2′-N-benzoylamino-phenyl)-indole.

M.P.: 176° C
Yield: 72%

EXAMPLE 19

2-(4′-Mercapto-phenyl)-indole

At a temperature between −35° C and −40° C, 20.7 g (0.9 mol) of sodium were added in one hour to a mixture containing 800 ml of liquid ammonia and 72.1 g (0.3 mol) of 2-(4′-methylthio-phenyl)-indole, prepared as described in Example 2.

In order to destroy the excess of sodium and the amide which formed ammonium chloride was added to the solution and the reaction medium was allowed to return to room-temperature until elimination of the ammonia.

The substance obtained was poured into an iced aqueous solution of hydrochloric acid and the solution was stirred for 12 hours.

The precipitate which formed was filtered out and washed with water until neutrality. After recrystallization from methanol 2-(4′-mercapto-phenyl)-indole was obtained.

M.P.: 238° C
Yield: 100% in crude product.

EXAMPLE 20

2-(4′-Butylthio-phenyl)-indole

To a mixture of 60 ml of N,N-dimethylformamide and 6.75 g (0.125 mol) of sodium methylate were added a solution of 60 ml of N,N-dimethylformamide containing 22.5 g (0.1 mol) of 2-(4′-mercapto-phenyl)-indole, prepared as described in Examples 2 or 19, after which were added at room-temperature and, drop-by-drop, 17.1 g (0.125 mol) of butyl bromide, the solution being vigorously stirred. Stirring was maintained for 2 hours and the reaction medium was poured into water.

The precipitate which formed was filtered out, washed with water until neutrality and purified by recrystallization from ethanol. Pure 2-(4′-butylthio-phenyl)-indole was obtained.

M.P.: 189°-191° C
Yield: 76%

By the above procedure but using the appropriate starting-products, the following compounds were prepared:

| Compounds | Melting Point |
| --- | --- |
| 2-(4′dodecylthio-phenyl)-indole | 185°/191° C (ethanol) |
| 2-(4′-isopropylthio-phenyl)-indole | 179° C (methanol-acetone 80/10) |
| 2-(4′-cyclohexylthio-phenyl)-indole | 179°/181° C (ethanol) |

EXAMPLE 21

2-(4′-Allyloxy-phenyl)-indole

To a mixture of 120 ml of N,N-dimethylformamide and 6.75 g (0.125 mol) of sodium methylate were added 20.9 g (0.1 mol) of 2-(4′-hydroxyphenyl)-indole, prepared as described in Example 2, after which were added, drop-by-drop, 15.1 g (0.125 mol) of allyl bromide. While stirring, the reaction mixture was heated to 60°-65° C for 1 hour and then to 100° C for 2 hours.

After cooling, the reaction medium was poured into water and extracted with ether. The ethereal phase was washed with water until neutrality, dried and then concentrated at reduced pressure. The mixture was recrystallized from benzene-methanol (70/30) and then purified by chromatography on a silica column with benzene as eluant.

Pure 2-(4′-allyloxy-phenyl)-indole was obtained.
M.P.: 214° C
Yield: 10% cm We claim:

1. New stabilizers of polyvinyl chloride and copolymers of vinyl chloride, the said stabilizers being 2-phenyl-indole derivatives corresponding to the following general formula:

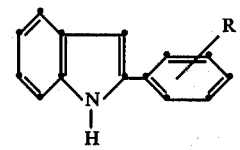

wherein R represents a phenyl group, an amino group, optionally substituted by an acetyl or benzoyl group, a mercapto group, optionally substituted by a branched- or straight-chain alkyl group containing from 1 to 12 carbon atoms or by a cyclohexyl radical, a carboxyl radical, a group $R_1O-$, wherein $R_1$ represents an atom of hydrogen, an isopropyl, carboxymethyl, carbethoxymethyl, carbethoxyisopropyl, acetyl, docosanoyl, benzoyl, benzyl, or allyl radical or a branched- or straight-chain alkyl radical containing from 6 to 12 carbon atoms.

2. 2-(4′-Dodecyloxy-phenyl)-indole.

3. Process for the preparation of the new stabilizers defined in claim 1 whereby a substituted acetophenone corresponding to the general formula:

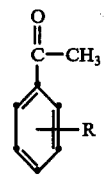

wherein R has the same meanings as in claim 1, is reacted with phenylhydrazine, and the resulting acetophenone phenylhyrazone is cyclised either by means of a dehydrating agent or by thermolysis to form the required 2-phenyl-indole derivative.

4. Process according to claim 3 whereby the operation of cyclisation is performed by means of polyphosphoric acid.

5. Process according to claim 3 whereby the operaton of cyclisation is performed by means of sulphuric acid.

6. Process for the preparation of the new stabilizers defined in claim 1 whereby a substituted acetophenone corresponding to the following general formula:

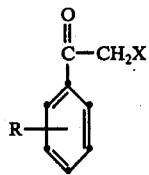

IV wherein R has the same meanings as in claim 1 and X represents an atom of halogen, is reacted with aniline to form the desired 2-phenyl-indole derivative.

7. Process according to claim 6 whereby the atom of halogen is an atom of chlorine or bromine.

8. Polyvinyl chloride and co-polymers of vinyl chloride containing at least one stabilizer as defined in claim 1.

9. Polyvinyl chloride and co-polymers as claimed in claim 8 which contain the said stabilizer in a proportion of 0.1% to 1% by weight.

* * * * *